(12) United States Patent
Reitblat et al.

(10) Patent No.: US 9,402,661 B2
(45) Date of Patent: Aug. 2, 2016

(54) LUMBAR-SACRAL SCREW INSERTION AND MANIPULATION

(71) Applicant: Stryker Spine, Cestas (FR)

(72) Inventors: Abram Reitblat, Monroe, NY (US); Steven Krause, Oakland, NJ (US)

(73) Assignee: Stryker European Holdings I, LCC, Kalamazoo, MI (US)

( * ) Notice: Subject to any disclaimer, the term of this patent is extended or adjusted under 35 U.S.C. 154(b) by 220 days.

(21) Appl. No.: 14/034,021

(22) Filed: Sep. 23, 2013

(65) Prior Publication Data

US 2015/0088210 A1   Mar. 26, 2015

(51) Int. Cl.
*A61B 17/70* (2006.01)
*A61B 17/02* (2006.01)

(52) U.S. Cl.
CPC ......... *A61B 17/7082* (2013.01); *A61B 17/7076* (2013.01); *A61B 17/0206* (2013.01); *A61B 17/7085* (2013.01)

(58) Field of Classification Search
CPC ........... A61B 17/7085; A61B 17/0206; A61B 17/7032
USPC ...................................... 606/86 A, 278, 86 R
See application file for complete search history.

(56) References Cited

U.S. PATENT DOCUMENTS

| | | | |
|---|---|---|---|
| 6,261,295 B1 * | 7/2001 | Nicholson .......... | A61B 17/1757 606/87 |
| 7,179,261 B2 | 2/2007 | Sicvol et al. | |
| 7,250,052 B2 * | 7/2007 | Landry .............. | A61B 17/1604 606/86 A |
| 7,491,208 B2 * | 2/2009 | Pond, Jr. ............ | A61B 17/7082 606/104 |
| 7,597,694 B2 | 10/2009 | Lim et al. | |
| 7,763,055 B2 | 7/2010 | Foley | |
| 7,811,288 B2 * | 10/2010 | Jones .................. | A61B 17/7091 606/279 |
| 7,846,093 B2 | 12/2010 | Gorek et al. | |
| 7,892,173 B2 * | 2/2011 | Miles ..................... | A61B 17/02 600/202 |
| 8,002,798 B2 * | 8/2011 | Chin .................. | A61B 17/7082 606/246 |
| 8,066,739 B2 * | 11/2011 | Jackson ............. | A61B 17/7008 606/246 |
| 8,162,952 B2 * | 4/2012 | Cohen .................. | A61B 17/708 606/104 |
| 8,177,817 B2 | 5/2012 | Fallin | |
| 8,469,960 B2 * | 6/2013 | Hutton ............... | A61B 17/7032 606/103 |
| 8,491,655 B2 * | 7/2013 | Adamo ................. | A61F 2/4425 606/279 |

(Continued)

FOREIGN PATENT DOCUMENTS

EP   2184022   5/2010
WO   2011123580 A1   10/2011

OTHER PUBLICATIONS

"MATRIX Spine System—MIS Instrumentation. A Minimally invasive instrument system for use with the MATRIX Spine System", Technique Guide, Synthes Spine, 2010, pp. 1-58.

(Continued)

*Primary Examiner* — Ellen C Hammond
*Assistant Examiner* — Stuart S Bray
(74) *Attorney, Agent, or Firm* — Lerner, David, Littenberg, Krumholz & Mentlik, LLP

(57) ABSTRACT

A method of percutaneous implantation of a pedicle screw system comprising the steps of implanting a first pedicle screw assembly in a first vertebra, the first pedicle screw assembly including a first coupling element connected with a first extension defining a first space and implanting a second pedicle screw assembly in a second vertebra, the second pedicle screw assembly including a second coupling element connected with a second extension and intersecting at least one a portion of the second extension with the first space.

12 Claims, 8 Drawing Sheets

(56) References Cited

U.S. PATENT DOCUMENTS

| | | | | |
|---|---|---|---|---|
| 8,795,167 B2* | 8/2014 | Ainsworth | A61B 17/0642 | 600/222 |
| 2005/0154389 A1* | 7/2005 | Selover | A61B 17/7074 | 606/914 |
| 2005/0245942 A1* | 11/2005 | DiPoto | A61B 17/3439 | 606/108 |
| 2006/0069391 A1* | 3/2006 | Jackson | A61B 17/7037 | 606/62 |
| 2006/0247630 A1* | 11/2006 | Iott | A61B 17/701 | 606/86 A |
| 2007/0049931 A1* | 3/2007 | Justis | A61B 17/7089 | 606/86 A |
| 2008/0077135 A1* | 3/2008 | Stad | A61B 17/8875 | 606/86 A |
| 2009/0149892 A1* | 6/2009 | Stad | A61B 17/7077 | 606/86 A |
| 2010/0004695 A1* | 1/2010 | Stad | A61B 17/7074 | 606/86 A |
| 2010/0030283 A1* | 2/2010 | King | A61B 17/7037 | 606/86 A |
| 2010/0114179 A1* | 5/2010 | Moore | A61B 17/7032 | 606/308 |
| 2011/0087293 A1* | 4/2011 | Ferreira | A61B 17/7088 | 606/265 |
| 2011/0184464 A1* | 7/2011 | Fiorella | A61B 17/7089 | 606/264 |
| 2011/0218581 A1* | 9/2011 | Justis | A61B 17/708 | 606/86 A |
| 2012/0035668 A1* | 2/2012 | Manninen | A61B 17/7037 | 606/305 |
| 2012/0101506 A1* | 4/2012 | Shim | A61B 17/0206 | 606/104 |
| 2013/0103096 A1* | 4/2013 | Miller | A61B 17/7032 | 606/305 |
| 2013/0289633 A1* | 10/2013 | Gleeson | A61B 17/708 | 606/86 A |
| 2014/0257416 A1* | 9/2014 | Meyer | A61B 17/7083 | 606/86 A |
| 2014/0277166 A1* | 9/2014 | Brinkman | A61B 17/7085 | 606/279 |
| 2014/0277206 A1* | 9/2014 | Reitblat | A61B 17/7085 | 606/86 A |
| 2014/0316475 A1* | 10/2014 | Parikh | A61B 17/7083 | 606/86 A |
| 2015/0157367 A1* | 6/2015 | Biedermann | A61B 17/7004 | 606/279 |
| 2015/0164495 A1* | 6/2015 | Petit | A61B 17/708 | 600/210 |
| 2015/0173810 A1* | 6/2015 | Biedermann | A61B 17/7088 | 606/279 |
| 2015/0335359 A1* | 11/2015 | May | A61B 17/708 | 606/86 A |

OTHER PUBLICATIONS

Extended European Search Report for Application No. EP14185888 dated Jan. 22, 2015.

* cited by examiner

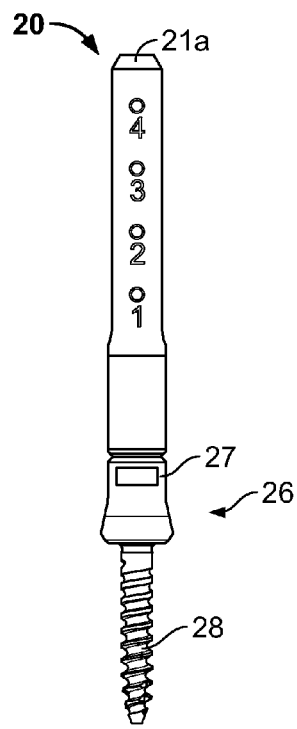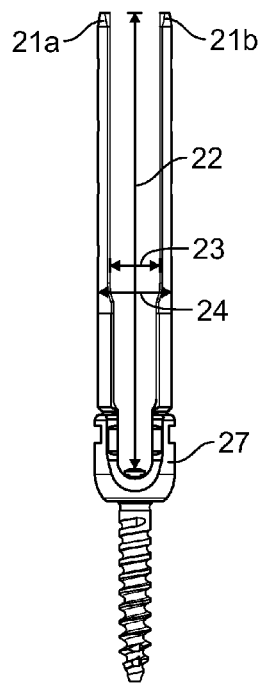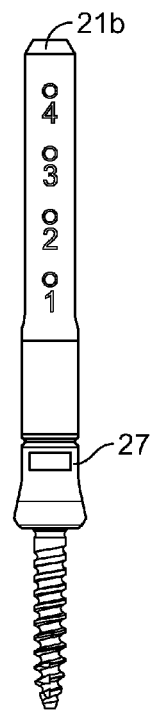
FIG. 2A  FIG. 2B  FIG. 2C
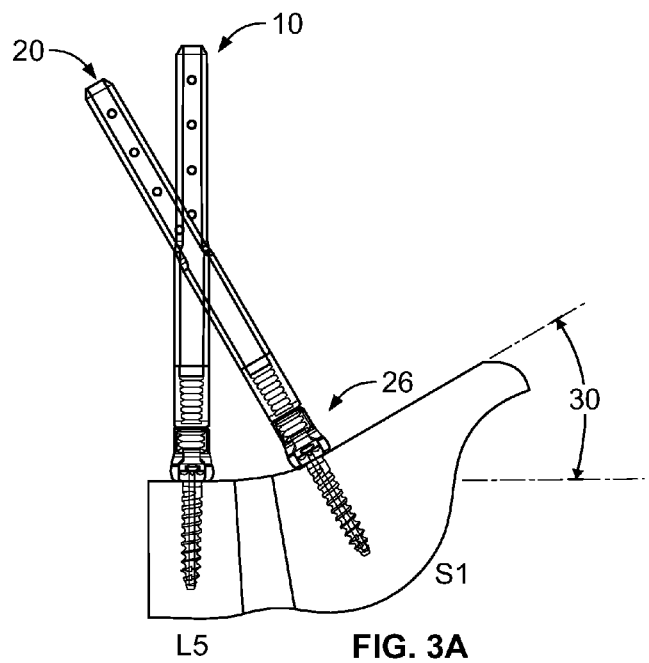
FIG. 3A

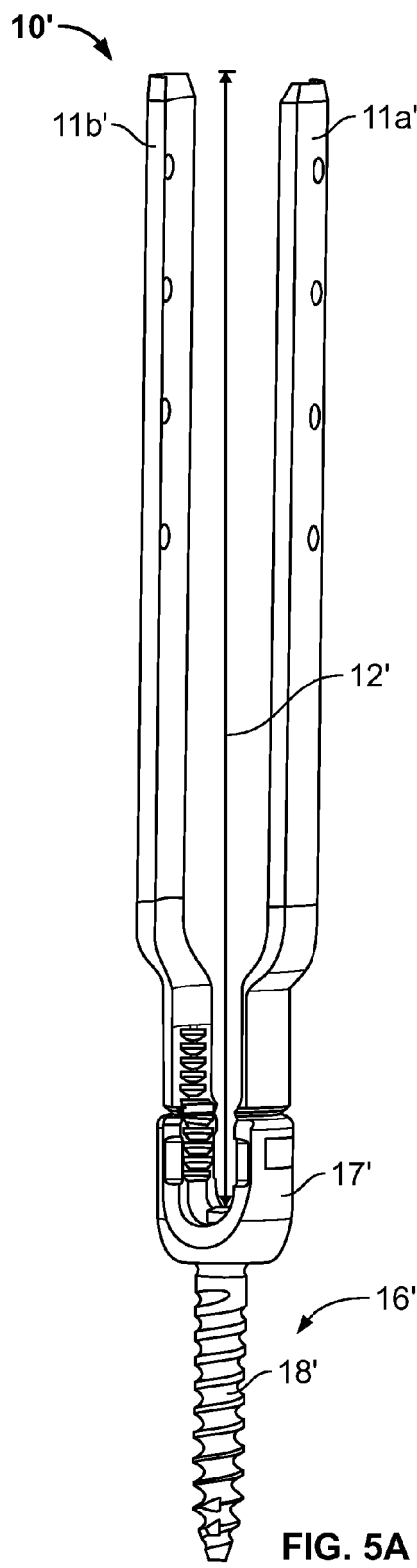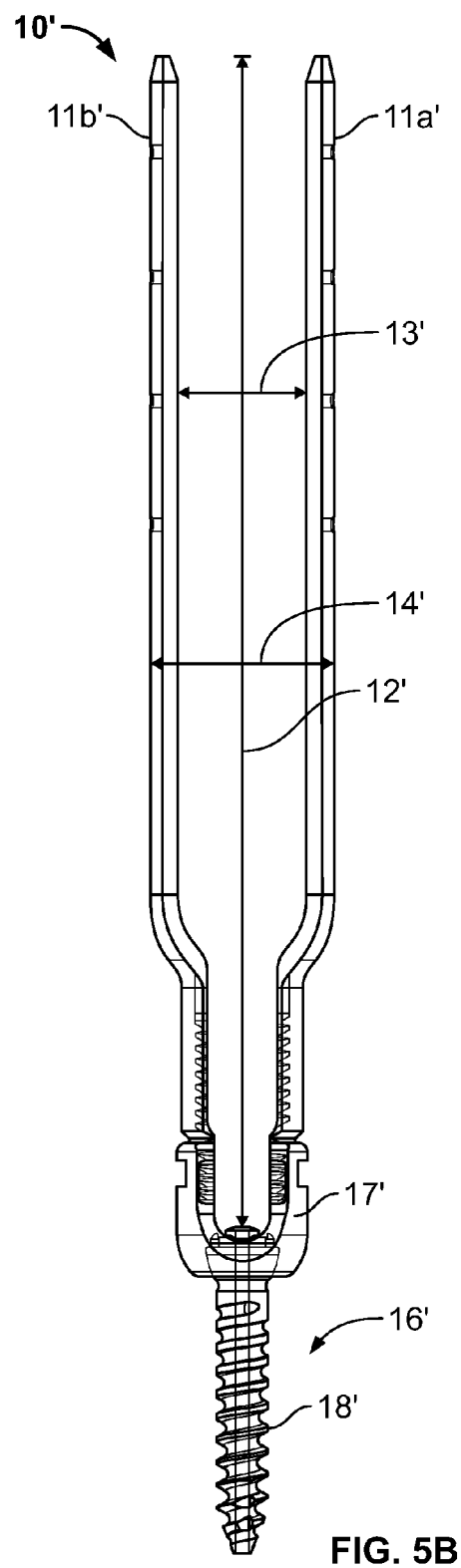
FIG. 5A
FIG. 5B

LUMBAR-SACRAL SCREW INSERTION AND MANIPULATION

BACKGROUND OF THE INVENTION

The present invention relates to devices and methods for minimally invasive pedicle screw placement, and more particularly to devices and methods that facilitate the fusion of vertebrae in the spine, for example the lumbar-sacral region of the spine during minimally invasive procedures.

In minimally invasive surgical procedures, which are becoming more and more prevalent, smaller incisions or portals are used to access the locations in the patient's body, which causes less trauma to the adjacent tissue, reduces recovery time and pain and may be performed in some cases under only local anesthesia. The avoidance of general anesthesia reduces post-operative recovery time and the risk of complications.

Minimally invasive surgical procedures are especially desirable for spine surgeries because spine pathologies are generally located in a part of the body without clear muscle planes and there exists a danger of damaging the adjacent neural and vascular tissues. For instance, in certain traditional spinal fixation procedures, the spinal muscles are stripped from the bony elements of the spine followed by laminectomy to expose the dura, the nerve roots, and the discs. The incision required to perform such a surgery has to be wide enough and the tissues have to be retracted to maintain a channel from the skin to the floor of the spinal canal that will allow direct visualization. Other non-minimally invasive fusion procedures may require more lateral tissue dissection and exposure to access the transverse processes and pedicles for placement of pedicle screws, rod constructs for stability, and bone grafts under direct vision.

To address these issues, minimally invasive spinal procedures have been developed, including in the placement of pedicle screws. One minimally invasive pedicle screw system is the MANTIS® system ("the Mantis System") offered by Stryker Spine of Allendale, N.J. (see U.S. Pat. No. 8,002,798, the entirety of which is hereby incorporated by reference herein). In that system, elongate blades are mechanically coupled to either side of the coupling element of each pedicle screw. Each such construct is implanted within the pedicle of a vertebra through a portal or small incision, rather than a larger more invasive incision. A rod is then percutaneously guided into the coupling elements of the implanted pedicle screws with help from the attached blades, again without the need for a larger more invasive incision. This system necessarily avoids the shortcomings of more invasive pedicle screw placement systems by reducing the area required to be incised and exposed. Stryker Spine also offers another minimally invasive pedicle screw system under the name ES2® system ("the ES2 System"), which differs from the Mantis System, inter alia, in the manner in which its blades are connected to its coupling elements (see U.S. Pat. No. 8,002,798, the entirety of which has been incorporated by reference herein). In the ES2 System, blades are integrally formed with coupling elements and are broken off after proper rod placement. Yet another percutaneous system is disclosed in U.S. Pat. No. 7,250,052 ("the '052 patent"), the disclosure of which is hereby incorporated by reference herein. There, detachable members or sleeves that include channels are disclosed as being useful in guiding a rod into two or more coupling elements. These systems (as well as others) all commonly utilize extensions of some sort that extend from the pedicle screws to aid in the percutaneous placement or minimally invasive introduction of a spinal rod into coupling elements.

A problem that occurs in such minimally invasive procedures for the spine often results from the natural curvature of the spine, for instance, in the lumbar-sacral region, which causes the instruments (e.g., the aforementioned extensions) used for such procedures to obstruct one another. This problem may also exist because of or be further exacerbated in situations where a patient exhibits lordotic deformities or because of the surgical technique (e.g., the surgeon's choice of insertion angle for the instruments), the shape and overall design of the instruments, or even the patient's orientation or placement on the operating surface. Oftentimes, the outwardly extending blades or other extensions on different pedicle screws may physically cross paths or project to cross paths and therefore obstruct one another or the channels for facilitating rod insertion. This issue is hereinafter referred to as clashing, and has, to date, only been addressed by inserting the screws with the blades (such as in the case of the Mantis and ES2 Systems) or other extensions (such as in the case of other existing percutaneous pedicle screw systems) attached at modified, less optimal angles to avoid one another.

Another common challenge encountered in minimally invasive surgical procedures is the implantation and manipulation of the rod through the screw extensions. Therefore, there exists a need for new extension geometries to improve the ease of rod insertion under any of various anatomical variations.

Thus, there is a need for a percutaneous pedicle screw delivery system and methodology which avoids the aforementioned clashing problems.

BRIEF SUMMARY OF THE INVENTION

The present disclosure is generally related to a percutaneous implant delivery system and a method of use thereof. In particular, the present disclosure is related to a percutaneous implant delivery system which facilitates the minimally invasive placement of pedicle screws and rods within a patient.

In an embodiment, a system for percutaneous implantation into bone is provided, the system including: a first pedicle screw assembly including a first coupling element connected with a first extension defining a first space having a first width therebetween; and a second pedicle screw assembly including a second coupling element connected with a second extension defining a second width between exterior surfaces thereof; wherein the first width is greater than the second width so that the second extension can fit within the first space.

In a further embodiment, a method of percutaneous implantation of a pedicle screw system comprising the steps of: implanting a first pedicle screw assembly in a first vertebra, the first pedicle screw assembly including a first coupling element connected with a first extension defining a first space; and implanting a second pedicle screw assembly in a second vertebra, the second pedicle screw assembly including a second coupling element connected with a second extension; and intersecting at least one a portion of the second extension with the first space.

BRIEF DESCRIPTION OF THE DRAWINGS

FIG. 2A is a front view of a second pedicle screw assembly.

FIG. 2B is a side view of the second pedicle screw assembly of FIG. 2A.

FIG. 2C is a rear view of the second pedicle screw assembly of FIG. 2A.

FIG. 3A is a cross-sectional side view of the first and second pedicle screw assemblies implanted into the L5 and S1 vertebrae, respectively.

FIG. 5A is a front-side view of a third pedicle screw assembly.

FIG. 5B is a cross-sectional front view of the third pedicle screw assembly of FIG. 5A.

DETAILED DESCRIPTION

Figure 1A:
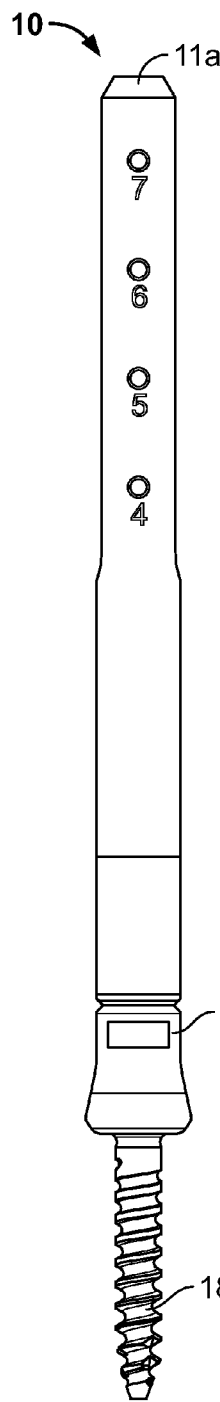
FIG. 1A is a front view of a first pedicle screw assembly.
Figure 1B:
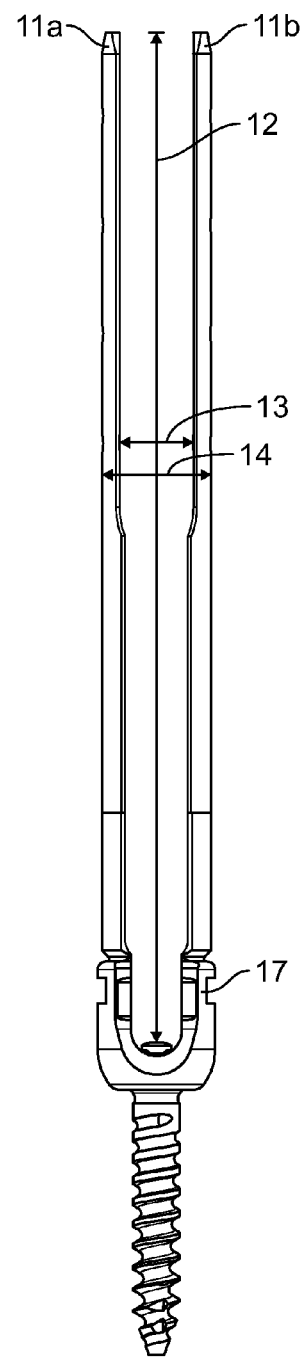
FIG. 1B is a side view of the first pedicle screw assembly of FIG. 1A.
Figure 1C:
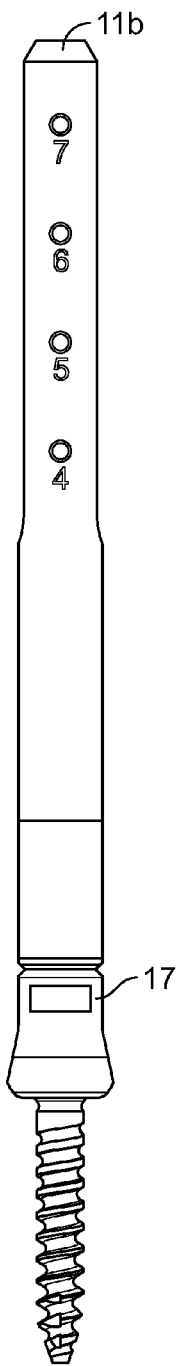
FIG. 1C is a rear view of the first pedicle screw assembly of FIG. 1A.

The present invention addresses the aforementioned problems faced by percutaneous pedicle screw assemblies, for instance, in areas of the spine where the curvature causes the pedicle faces of adjacent vertebrae to face towards one another (e.g., the lumbar-sacral region of the spine). Although the present invention is not limited to any particular percutaneous pedicle screw system, certain embodiments described in the following description incorporate elements from the Mantis and ES2 Systems. Of course, the present application has applicability to other percutaneous pedicle screw systems that may employ differently structured components extending from the pedicle screws, such as systems in which tubular components having slots or channels formed therethrough are connected with coupling elements (e.g., as in the '052 patent).

FIGS. 1A-1C and 2A-2C depict first and second pedicle screw assemblies 10, 20. Again, although such assemblies are similar to components included in the ES2 System, these components are merely exemplary and other designs can be utilized in accordance with the present invention. Assembly 10 includes two blades 11a and 11b secured to opposing sides of a coupling element 17 of a pedicle screw 16 in order to define a space 12 having a width 13 therebetween. As shown, blades 11a and 11b are integrally formed with coupling element 17, in a manner that allows the blades to be removable therefrom. The relationship between coupling element 17 and a screw portion 18 may resemble that of any type of pedicle screw, for instance, the components as shown are polyaxially associated with one another.

As shown in FIGS. 2A-2C, assembly 20 includes two blades 21a and 21b secured to opposing sides of a coupling element 27 of a pedicle screw 26 in order to define a space 22 having a width 23 therebetween. As shown, blades 21a and 21b are integrally formed with coupling element 27, in a manner that allows the blades to be removable therefrom. The relationship between coupling element 27 and a screw portion 28 may resemble that of any type of pedicle screw, for instance, the components as shown are polyaxially associated with one another.

In other embodiments, it is envisioned that aforementioned blades may be secured to the coupling element in a different fashion. For example, in the case of the Mantis System, the blades are mechanically secured to the coupling element such that they may be removed and reattached thereto. Again, it is also entirely within the scope of this invention to utilize a different extension component associated with the pedicle screw coupling element, such as the detachable members or sleeves disclosed in the '052 patent. Furthermore, although pedicle screws 16 and 26 are of a similar type, it is to be understood that assemblies 10 and 20 may include differently configured or differently sized pedicle screws. Likewise, the assemblies need not include the same type of extension component. For instance, assembly 10 may be akin to the screws of the ES2 System, while assembly 20 may be akin to the Mantis system.

Figure 5C:
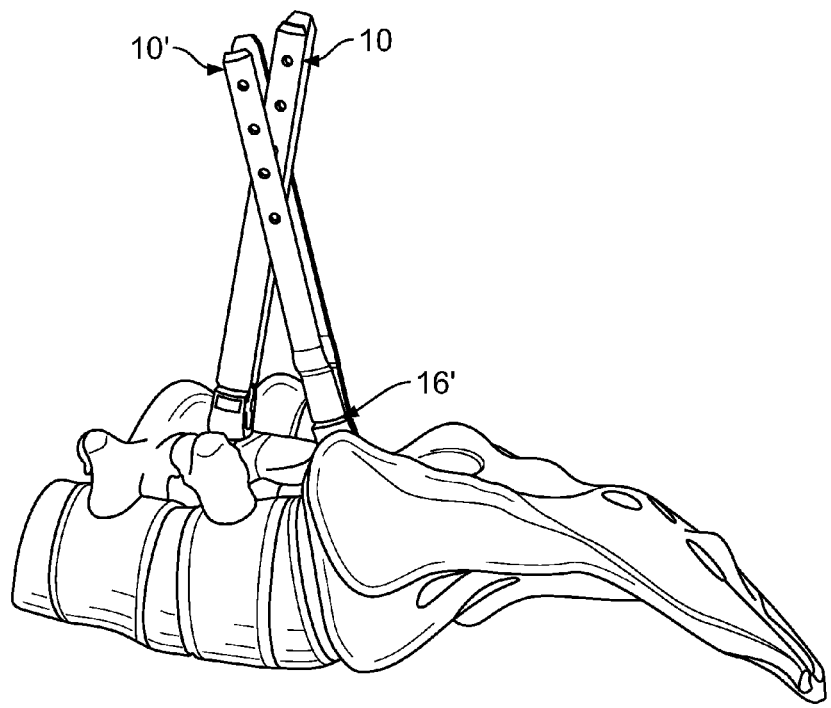
FIG. 5C is a side view of the first and third pedicle screw assemblies implanted into the L5 and S1 vertebrae, respectively.

It is to be understood that any of widths 13, 23 or distances 14, 24, as well as the lengths of the blades 11a, 11b, 21a, 21b themselves, may vary. However, in a preferred embodiment, widths 13 and 23 are approximately 8.8 mm and distances 14 and 24 are approximately 13 mm. In other embodiments, widths 13 and 23 may range from 6 to 12 mm and distances 14 and 24 may range from 8 to 20 mm. Thus, assemblies 10 and 20 are shown as being identical in at least these dimensions (blades 21a and 21b do exhibit a different height than blades 11a and 11b). It is to be understood, that differently configured assemblies can be provided in accordance with the present invention. For instance, as is shown in below discussed assembly 10', the distance between the interior of the blades (shown in FIGS. 5A and 5B as element 13') can be greater than that of the exterior of another assembly.

Figure 3B:
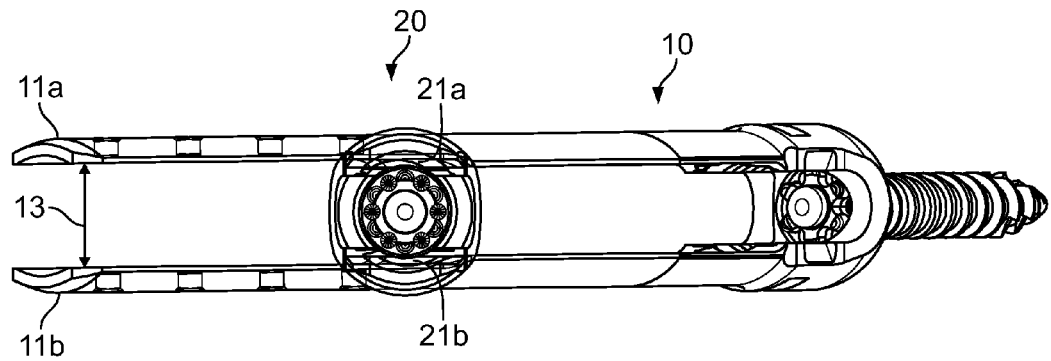
FIG. 3B is a cross-sectional top view of the configuration of FIG. 3A.

In an exemplary method of use, as shown in FIGS. 3A and 3B, first assembly 10 is engaged with the pedicle of a first vertebra, for example, the L5 vertebra, and second assembly 20 is engaged with the pedicle of a second vertebra, for example the S1 vertebra. It is to be understood that the engagement of the assemblies with the respective vertebrae can be performed according to any known methodology, including insertion through small portals formed adjacent each vertebrae to be implanted, or even through a single incision. After engagement of the screw portions 18, 28 with the respective vertebrae, as shown in FIG. 3A, the blades of assemblies 10, may be disposed towards each other, such that their paths intersect. This is at least due in part to the anatomy of the L5-S1 region. Given the similarity between assemblies 10 and 20, one set of blades can be flexed outwardly to thereby increase its interior width 13 or 23. With the blades flexed in this manner, the other set can be placed therebetween. However, in other embodiments (such as in the below-discussed assembly 10'), the width between one set of blades may be such that an adjacent, narrower set of blades may be placed therebetween, without the need to flex any of the blades outwardly. In any event, FIGS. 3A and 3B depict an illustrative scenario where one set of blades (blades 21a, 21b) are placed between another set of blades (blades 11a, 11b). Thus, the clashing problem that would otherwise be present in conventional percutaneous pedicle screw systems is overcome.

With assemblies in the above-discussed position, the remainder procedure may be performed. This includes, inter alia, percutaneously placing a rod, which may be contoured before insertion to match the desired localized curvature of the spine, which ultimately spans between the two assemblies. One such contouring procedure is disclosed in U.S. Pat.

No. 8,177,817, the disclosure of which is hereby incorporated by reference herein. Because of their positioning, blades 11a, 11b and 21a, 21b may still be utilized to guide the rod into place. In addition, the blades may also still aid in the securement of the rod by, for example, allowing for the placement of a set screw or other fixation means. Ultimately, blades 11a, 11b, 21a and 21b are removed from pedicle screws 30.

Figure 4A:
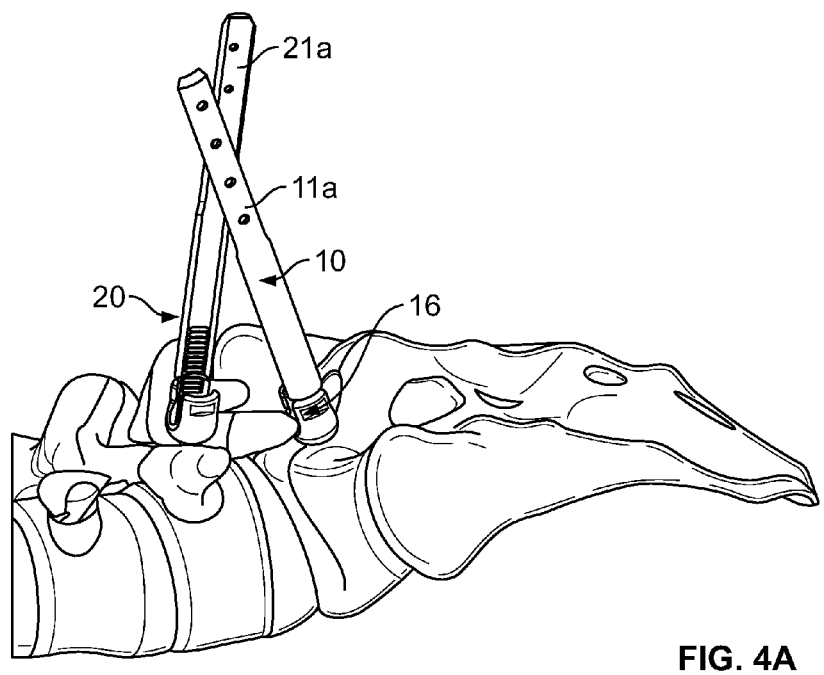
FIG. 4A is a side view of the first and second pedicle screw assemblies implanted into the L5 and S1 vertebrae, respectively, with a blade from each assembly removed.
Figure 4B:
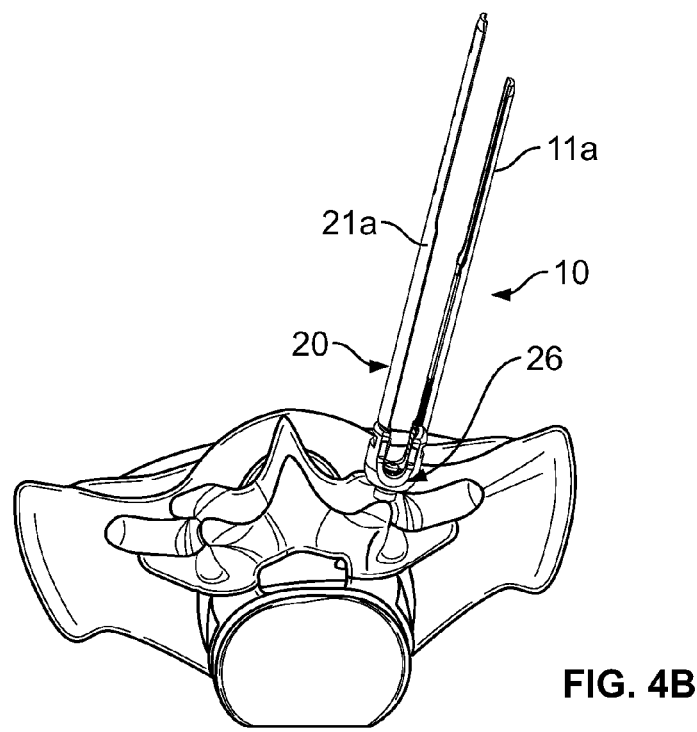
FIG. 4B is a front view of the configuration of FIG. 4A.
Figure 4C:
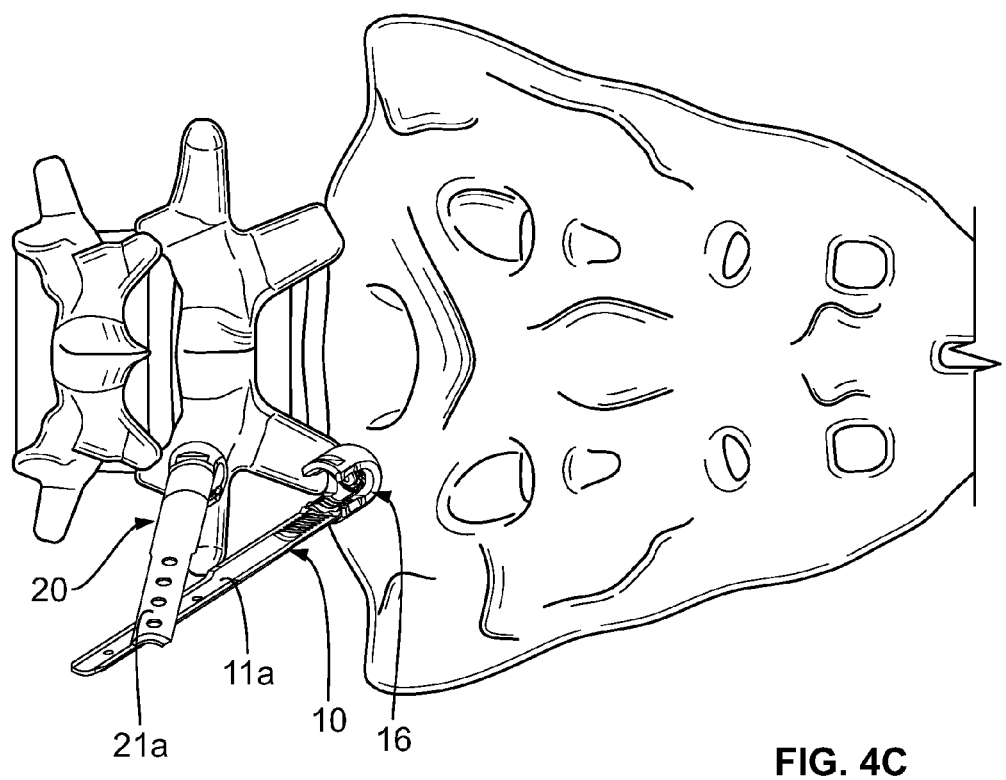
FIG. 4C is a top view of the configuration of FIG. 4A.

In an alternative embodiment of the method, as shown in FIGS. 4A-4C, the clashing problem may be avoided by selectively detaching one or more of blades 11a, 11b, 21a, or 21b from the pedicle screws 16, 26. For example, if after implantation of assemblies 10 and 20, two of the blades obstruct one another, the surgeon may detach one of them to avoid the conflict. As shown in FIGS. 4A-4C, it is envisioned that the surgeon may even detach multiple intersecting blades in such an instance (i.e., blades 11b and 21b are shown removed). The remaining blades effectively create a channel which may be relied upon to guide the percutaneous insertion of a rod into the implanted pedicle screws 16, 26. Because this method involves the removal of intersecting blades, the method may even be used with just one model of a pedicle screw assembly, having the same dimensions for each assembly, by detaching one or both intersecting blades of adjacently implanted assemblies.

Because the natural or deformed curvature of a spine may vary, the point and angle at which the blades of one assembly intersect with the blades of another assembly may vary on a case-by-case basis. However, the blades themselves are generally unrestricted from intersecting one another at any angle. Additionally, depending on the method employed, as well as the widths of the intersecting assemblies and the angles at which they are implanted into the patient, the blades of one assembly may or may not contact the blades of the other when their paths intersect one another.

In order to increase the range of widths at which the blades of the assemblies may intersect one another, the alternative embodiment of FIGS. 5A and 5B is envisioned. The widened pedicle screw assembly 10' includes two blades 11a' and 11b' which may be integrally or mechanically secured (shown integrally secured) to opposing sides of a coupling element 17' of a pedicle screw 16' in order to define a space 12' therebetween. A distance 14' is defined by the space between opposing points on the exteriors of the blades 11a', 11b', while space 12' has a width 13'. As in the above assemblies, pedicle screw 16' may be any type of pedicle screw, e.g., a screw portion 18' may be polyaxially associated with coupling element 17'.

Figure 5D:
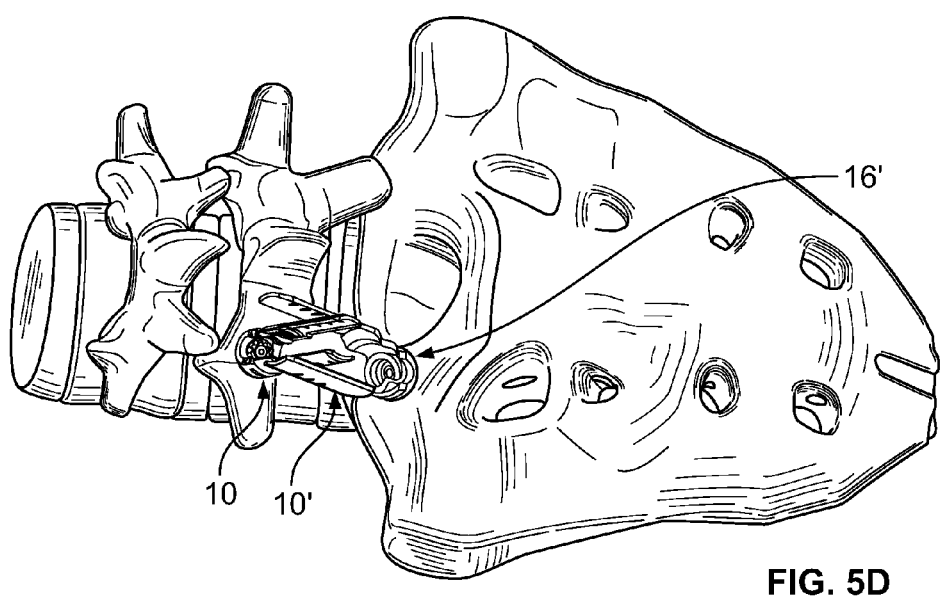
FIG. 5D is a top view of the configuration of FIG. 5C.

Because an upper portion of blades 11a' and 11b' may extend along a different plane than that of the coupling element 31 to which the blades 11a', 11b' are attached, assembly 10' allows for a wider width 13' and distance 14' than those defined by the dimensions of the coupling element 31 to which the blades 11a', 11b' are attached. In a preferred embodiment of assembly 10', width 13' is approximately 14 mm and distance 14' is approximately 19 mm. In alternate embodiments, width 13' may range from 10-20 mm and distance 14' may range from 15-25 mm. In yet another alternate embodiment, it is even envisioned that blades 11a', 11b' may follow different planes along their respective lengths, such that the distance 14' between the blades may transition into broader or narrower distances along the length of the blades. Thus, assembly 10' may be used in lieu of assemblies 10 (see FIGS. 5C and 5D) or 20 (not shown), or both (not shown), for the aforementioned methods of use in order to increase the range of widths by which the blades may intersect. However, it is to be understood that any of widths 13, 13', 23 or distances 14, 14', 24 may vary, as well as the lengths of the blades 11a, 11b, 11a', 11b', 21a, 21b themselves. It is also envisioned that the blades 11a, 11b, 11a', 11b' 21a, 21b may be interchangeable as the situation dictates, such that a single pedicle screw assembly may feature a combination of blades 11a and 21a, or 21b and 11b', and so forth.

Figure 5E:
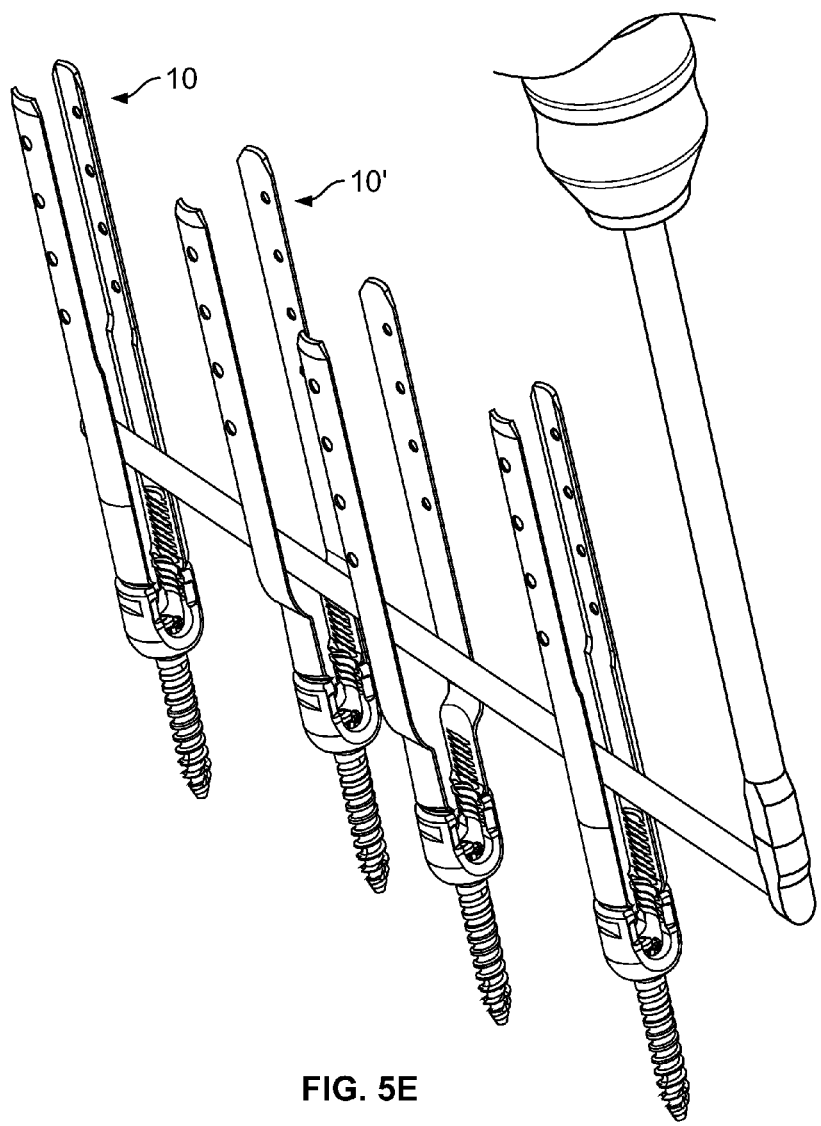
FIG. 5E is a perspective view of a rod being inserted into four pedicle screw assemblies.
Figure 5F:
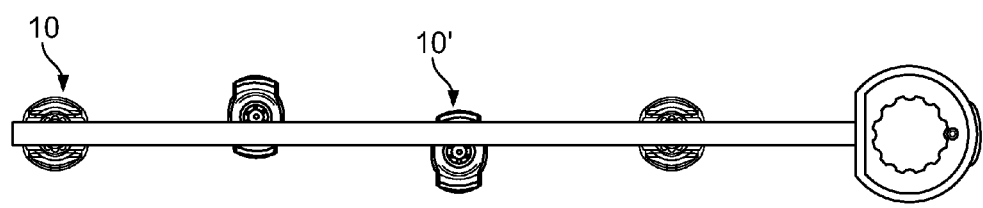
FIG. 5F is a top view of the configuration of FIG. 5E.

Additionally, once the assemblies are implanted, the larger width 13' of assembly 10' provides a broader tolerance for manipulation of the rod, thereby easing its insertion into the implanted coupling elements. In other words, assembly 10' is not only useful in instances where clashing is present, but also in instances where the pedicle screws may be displaced laterally/medially from each other. As shown in FIGS. 5E and 5F, the larger widths of the two assemblies 10' which are provided allow for the rod to be percutaneously inserted, even though those assemblies are offset from assemblies 10, also shown in the figure. Thus, the present invention not only is useful in preventing clashing, but also in aligning a rod during percutaneous insertion.

Figure 6:
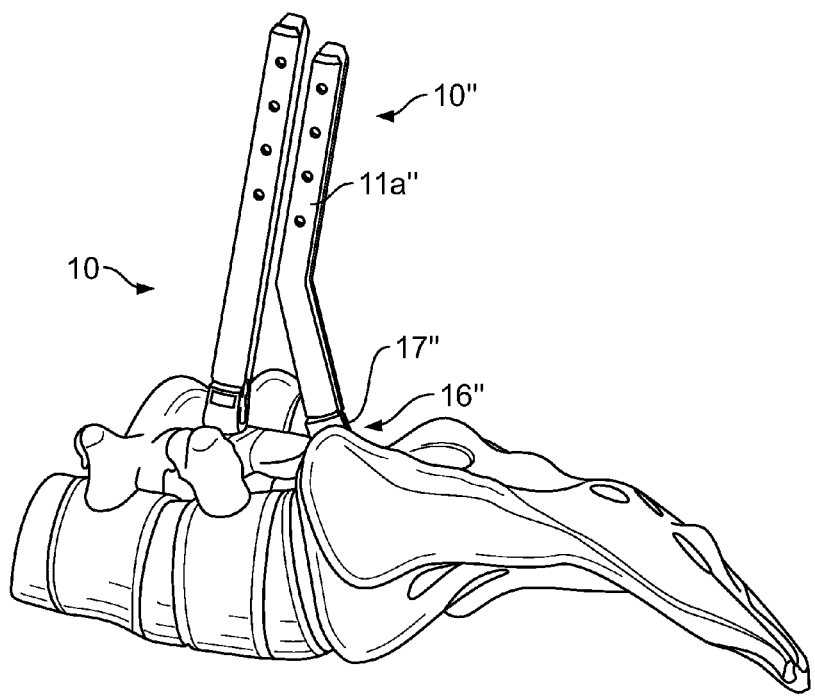
FIG. 6 is a side view of the first pedicle screw assembly and a fourth pedicle screw assembly implanted into the L5 and S1 vertebrae, respectively.

Yet another alternative embodiment pedicle screw assembly 10" is shown in FIG. 6, implanted adjacent to pedicle screw assembly 10. The curved pedicle screw assembly 10" includes two blades 11a" and 11b" (the latter of which is not shown) that may be integrally or mechanically secured (shown integrally secured) to opposing sides of a coupling element 17" of a pedicle screw 16' in order to define a space therebetween. Like in the above-discussed assemblies, width 13" and distance 14", respectively are defined between opposing points on the interiors and exteriors of the blades 11a", 11b". Also, as in the above-discussed embodiments, pedicle screw 16" may be any type of pedicle screw, e.g., a screw portion 18" (not shown) may be polyaxially associated with the coupling element 17".

Blades 11a", 11b" of assembly 10" are curved at a point along their respective lengths. Thus, when implanted, the coupling element 17" may be positioned such that the blades 11a", 11b" attached thereto are curved away from the blades of an adjacently implanted assembly. Thus, the curved assembly 10" provides an extra channel to facilitate rod insertion without clashing with the blades of the adjacent pedicle screw assembly.

Depending on doctor and patient needs, it is envisioned that the curved assembly 10" may bend along any point of the lengths of the blades 11a", 11b" (as shown in FIG. 6) or curve along any portion of the lengths, or any combination of the aforementioned characteristics. In addition, although the curved assembly 10" in FIG. 6 is implanted adjacent pedicle screw assembly 10, the curved assembly 10" may be utilized with any of the aforementioned assemblies 10, 20, 10', including another curved assembly 10".

Figure 7:
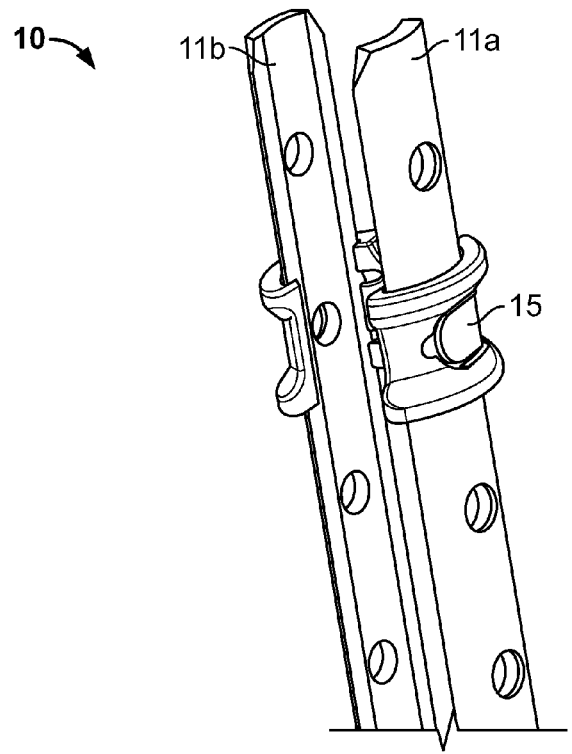
FIG. 7 is a perspective view of a clip secured to the pedicle screw assembly of FIG. 1A.

As shown in FIG. 7, any of the blades heretofore discussed may be further secured by a clip 15, like that currently utilized in the ES2 System. For instance, clip 15 is shown in FIG. 7 fixedly or slidably secured to a portion along the lengths of blades 11a, 11b in order to prevent deflection of the blades 11a, 11b about their engagements with the coupling element 17. In addition to reinforcing the engagement of the blades 11a, 11b with the coupling element 17, the clip 15 may also be used to aid the surgeon or other medical professional in properly contouring a rod before implantation into the patient. By placing a clip on each implanted assembly along a plane parallel to the patient's spine, the operator may determine the curvature necessary for the rod to be implanted before percutaneously inserting said rod. Although the clip 15 shown is sized to attach to the blades 11a, 11b of assembly 10, the clip may be sized to attach to the blades of any range of distances or widths in the same manner.

Although polyaxial pedicle screws are utilized in the above-discussed embodiments, fixed, monolithic or uniplanar screws, polyaxial hooks or the like may be employed. Similarly, a rod is discussed above as being used in the preferred embodiments, but the connecting device may be plates, rods, wires or articulating versions thereof. In addition, although not discussed specifically above, more than two pedicle screw assemblies may be implanted in a given surgery and different areas of the spine may also make use of the present invention. For instance, the screw assemblies may be implanted into a three-vertebrae construct including the L5-S1 region and, in certain extreme cases of deformity or disease, other areas of the spine, other than the L5-S1 region may even benefit from the present invention.

Moreover, as noted above, the present invention has applicability to systems that employ tubular elements having slots or channels formed therethrough. In such a case in accordance with the present invention, the slot or channel of one such component would be sized to accept at least a portion of the other tubular component. Put differently, the outer diameter or dimension of one tubular element would be smaller than the slot or channel of the other tubular element. A method of utilizing such an embodiment would follow as described above.

Still further, the present invention may have applicability to systems in which intervertebral fusion is also accomplished. For instance, it is commonplace for both pedicle screws and intervertebral devices, including fusion biologic devices comprising biologically created materials which can promote bone growth, to be utilized in the same surgery. This has the benefit of effecting not only posterior fixation, but also fixation between the vertebral bodies as well.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for percutaneous implantation into bone, the system comprising:
    a first pedicle screw assembly including a first coupling element connected with a first extension, the first extension including a first blade and a second blade defining a first space having a first width therebetween, the first and second blades each having a length between a distal end and a proximal end, the distal end of each of the first and second blades being connected with the first coupling element; and
    a second pedicle screw assembly including a second coupling element connected with a second extension defining a second width between exterior surfaces thereof;
    wherein the first width is greater than the second width so that the second extension can fit within the first space;
    wherein, the distal end of the first blade extends along a first longitudinal axis, and the distal end of the second blade extends along a second longitudinal axis,
    wherein, independent of deformation of either of the first or second blades, the first blade deviates from the first longitudinal axis along the length of the first blade, and the second blade deviates from the second longitudinal axis along the length of the second blade; and wherein the proximal end of the first blade extends along a third longitudinal axis, and the proximal end of the second blade extends along a fourth longitudinal axis; wherein the first extension has a central longitudinal axis; and wherein the third longitudinal axis of the proximal end of the first blade is spaced further away from the central longitudinal axis than the first longitudinal axis of the distal end of the first blade, and the fourth longitudinal axis of the proximal end of the second blade is spaced further away from the central longitudinal axis than the second longitudinal axis of the distal end of the second blade.

2. The system for percutaneous implantation of claim 1, wherein the second extension includes third and fourth blades.

3. The system for percutaneous implantation of claim 2, wherein the first and second blades are integrally formed with the first coupling element.

4. The system for percutaneous implantation of claim 3, wherein the third and fourth blades are mechanically coupled with the second coupling element.

5. The system for percutaneous implantation of claim 3, wherein the third and fourth blades are integrally formed with the second coupling element.

6. The system for percutaneous implantation of claim 2, wherein the first and second blades are mechanically coupled with the first coupling element.

7. The system for percutaneous implantation of claim 6, wherein the third and fourth blades are mechanically coupled with the second coupling element.

8. The system for percutaneous implantation of claim 6, wherein the third and fourth blades are integrally formed with the second coupling element.

9. The system for percutaneous implantation of claim 2, further comprising a first clip attached to a portion of the first and second blades.

10. The system for percutaneous implantation of claim 9, further comprising a second clip attached to a portion of the third and fourth blades.

11. The system for percutaneous implantation of claim 1, wherein the first and second blades are curved.

12. The system for percutaneous implantation of claim 1, wherein the third longitudinal axis is spaced further away from the central longitudinal axis than the first longitudinal axis by a first laterally outward step of the first blade, and wherein the fourth longitudinal axis is spaced further away from the central longitudinal axis than the second longitudinal axis by a second laterally outward step of the second blade.

* * * * *